US00PP24036P3

(12) United States Plant Patent
Egger

(10) Patent No.: US PP24,036 P3
(45) Date of Patent: Nov. 19, 2013

(54) ***KNIPHOFIA* PLANT NAMED 'REDHOT POPSICLE'**

(50) Latin Name: ***Kniphofia* spp.**
Varietal Denomination: Redhot Popsicle

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 79 days.

(21) Appl. No.: 13/506,430

(22) Filed: Apr. 17, 2012

(65) Prior Publication Data

US 2013/0276198 P1 Oct. 17, 2013

(51) Int. Cl.
*A01H 5/00* (2006.01)

(52) U.S. Cl.
USPC ..... Plt./443

(58) Field of Classification Search
USPC ..... Plt./443
See application file for complete search history.

*Primary Examiner* — Annette Para
(74) *Attorney, Agent, or Firm* — Klarquist Sparkman, LLP

(57) ABSTRACT

A new and distinct *Kniphofia* plant characterized by its numerous spikes of coral red flowers the first year, repeat blooming from June through September in Canby, Oreg., a compact habit with multiple crowns, narrow, grassy leaves, and excellent vigor.

1 Drawing Sheet

Botanical denomination: *Kniphofia* spp.
Cultivar designation: Redhot Popsicle.

BACKGROUND OF THE INVENTION

The present invention relates to a new and distinct *Kniphofia*, and given the cultivar name is 'Redhot Popsicle'. *Kniphofia* is in the family Asphodelaceae. 'Redhot Popsicle' is a hybrid resulting from a planned breeding program to produce a series of compact, reblooming *Kniphofia*. The cross was made using the following proprietary, unreleased plants: *Kniphofia* 26-1, as the seed parent, and *Kniphofia* 20-1, as the pollen parent. It was selected for best habit, flower color, reblooming, and crown count from many seedlings of the cross in Canby, Oreg.

Compared to *Kniphofia* 'Bressingham Comet' (an unpatented plant), the new cultivar is more free flowering with red flowers rather than yellow to red orange flowers.

Compared to *Kniphofia* 'Nancy's Red' (an unpatented plant), the new cultivar is shorter and much more free flowering.

SUMMARY OF THE INVENTION

The new cultivar is unique and characterized by:

1. numerous spikes of coral red flowers the first year
2. repeat blooming from June through September in Canby, Oreg.
3. compact habit with multiple crowns
4. narrow, grassy leaves
5. excellent vigor, fills a one gallon pot the first year from tissue culture This new cultivar has been reproduced only by asexual propagation (division, tissue culture). Each of the progeny exhibits identical characteristics to the new cultivar. Asexual propagation by leaf cuttings, tissue culture, and division using standard techniques as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a plant of a one-year-old *Kniphofia* 'Redhot Popsicle' in the ground in the trial field in July in Canby, Oreg.

DETAILED PLANT DESCRIPTION

The following is a detailed description of the new *Kniphofia* cultivar based on observations of six-month-old specimens growing in the ground outside in part sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, 5$^{th}$ edition.

Plant:

*Type.*—Rhizomatous herbaceous perennial.
*Hardiness.*—USDA Zones 6 to 9.
*Size.*—Grows to 41 cm wide and 34 cm tall from the top of the soil to the top of the foliage.
*Form.*—Upright and clumping.

Leaf:

*Type.*—Simple.
*Shape.*—Strap-like.
*Arrangement.*—Basal rosette.
*Blade size.*—Grows to 40 cm long and 10 mm wide.
*Margins.*—Serrulate.
*Apex.*—Acuminate.
*Base.*—Clasping.
*Surface texture.*—Glabrous on both surfaces.
*Venation.*—Parallel.
*Color.*—Top and bottom side Green 137A.

Inflorescence:

*Type.*—Spike-like scapose raceme.

*Number of flowers per raceme.*—About 100.

*Inflorescence.*—Grows to 25 cm long and 5 cm wide.

*Peduncle description.*—Grows to 35 cm long and 7 mm wide, glabrous to glaucous, Yellow Green 146C.

*Pedicle description.*—2.5 mm long, glabrous, Greyed Orange 177D.

*Bloom time.*—Late June through September in Canby, Oreg.

*Lastingness.*—An inflorescence lasts for 2 to 4 weeks depending on the temperatures.

Flower Bud:

*Size.*—26 mm long and 5 mm wide.

*Shape.*—Cylindrical.

*Surface texture.*—Glabrous.

*Color.*—Orange Red N34C.

Flower:

*Type.*—Actinomorphic.

*Shape.*—Cylindrical and tubular.

*Size.*—Grows to 4 cm deep and 12 mm wide.

*Texture.*—Waxy.

*Surface texture.*—Glabrous inside and outside.

*Color.*—Outside, Orange Red N34C, inside Red 35A with veins Orange Red N34A.

*Corolla description.*—6 lobed fused tepals, 27 mm long and 12 mm wide, each lobe 3 mm to 3.5 mm wide and 5 mm long, ovate to oblong, margin entire, tip notched; glabrous inside and out.

*Pistil description.*—One extruding, 33 mm long, ovary 3 mm long 1.8 mm wide, Yellow Green 144A, style 30 mm long, Red 36D, stigma White 155A.

*Stamen.*—6, 34 mm long, filaments 33 mm long, and Yellow 4D, anthers 1.5 mm long and Yellow 13A, pollen Yellow 4B.

*Fragrance.*—None.

Fruit and seed: None seen.

Pest and diseases: No known resistances to pests or diseases. No problems have been observed on this plant grown under commercial conditions in Canby, Oreg.

I claim:

1. A new and distinct *Kniphofia* plant as herein shown and described.

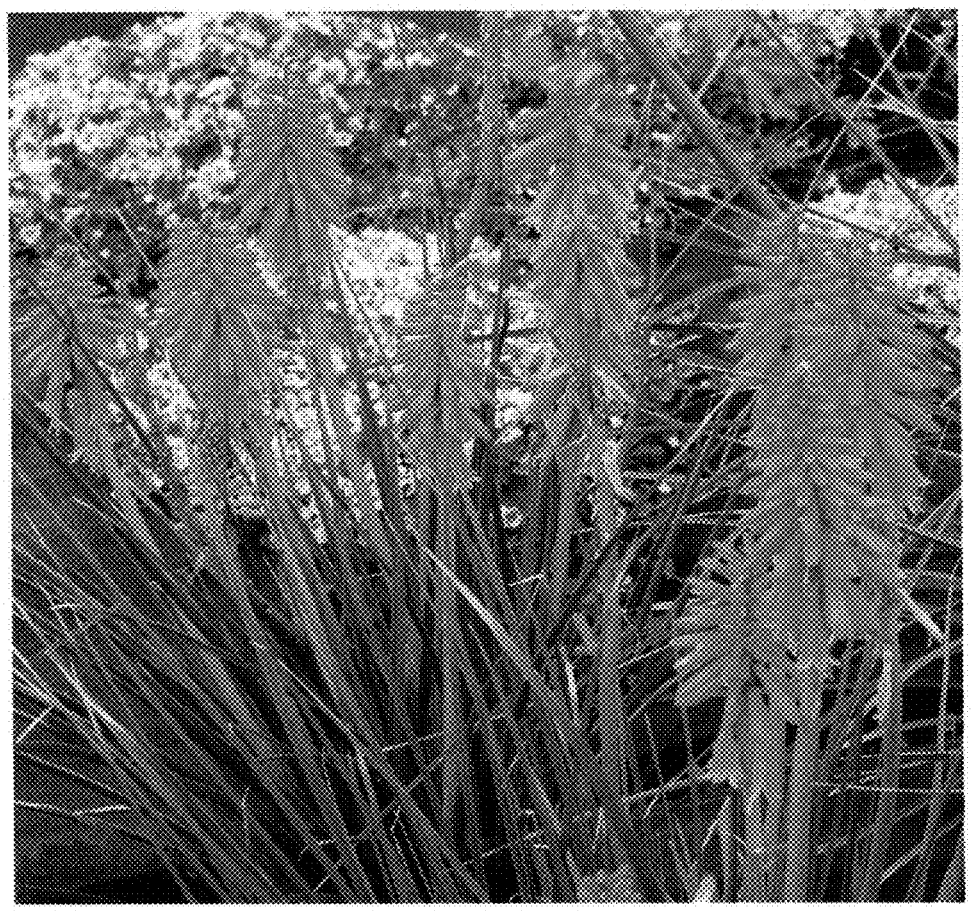

* * * * *